US011160837B2

(12) United States Patent
Zou et al.

(10) Patent No.: US 11,160,837 B2
(45) Date of Patent: Nov. 2, 2021

(54) MEGAMONAS FUNIFORMIS AND APPLICATIONS THEREOF

(71) Applicant: BGI SHENZHEN, Guangdong (CN)

(72) Inventors: Yuanqiang Zou, Guangdong (CN); Liang Xiao, Guangdong (CN); Xiaoping Li, Guangdong (CN); Jinghong Yu, Guangdong (CN); Chuan Liu, Guangdong (CN)

(73) Assignee: BGI SHENZHEN, Guangdong (CN)

( * ) Notice: Subject to any disclaimer, the term of this patent is extended or adjusted under 35 U.S.C. 154(b) by 0 days.

(21) Appl. No.: 16/647,344

(22) PCT Filed: Sep. 15, 2017

(86) PCT No.: PCT/CN2017/101915
§ 371 (c)(1),
(2) Date: Mar. 13, 2020

(87) PCT Pub. No.: WO2019/051790
PCT Pub. Date: Mar. 21, 2019

(65) Prior Publication Data
US 2020/0384039 A1 Dec. 10, 2020

(51) Int. Cl.
| | |
|---|---|
| A61K 35/741 | (2015.01) |
| A23L 33/175 | (2016.01) |
| A23L 33/15 | (2016.01) |
| A23L 33/135 | (2016.01) |
| A23L 33/00 | (2016.01) |
| A61P 3/06 | (2006.01) |
| A61P 1/00 | (2006.01) |
| A61P 29/00 | (2006.01) |
| A61K 9/00 | (2006.01) |
| C12N 1/20 | (2006.01) |

(Continued)

(52) U.S. Cl.
CPC .......... *A61K 35/741* (2013.01); *A23L 33/135* (2016.08); *A23L 33/15* (2016.08); *A23L 33/175* (2016.08); *A23L 33/40* (2016.08); *A61K 9/0056* (2013.01); *A61P 1/00* (2018.01); *A61P 3/06* (2018.01); *A61P 29/00* (2018.01); *C12N 1/205* (2021.05); *A23V 2002/00* (2013.01); *A61K 2035/115* (2013.01); *C12R 2001/01* (2021.05)

(58) Field of Classification Search
CPC .................................................. A61K 35/741
See application file for complete search history.

(56) References Cited

U.S. PATENT DOCUMENTS

2016/0039944 A1* 2/2016 Shinkura ................. A61P 31/04
424/139.1

FOREIGN PATENT DOCUMENTS

| CN | 104546938 | 4/2015 |
| CN | 105950780 | 9/2016 |

OTHER PUBLICATIONS

"Uncultured bacterium clone SJTU_D_01_66 16S ribosomal RNA gene, partial sequence," Database EMBL, Accession No. EF400799.
(Continued)

*Primary Examiner* — Rosanne Kosson
(74) *Attorney, Agent, or Firm* — Hodgson Russ LLP

(57) ABSTRACT

Provided are *Megamonas funiformis* and applications thereof. Specifically, the *Megamonas funiformis* has the effects for preventing and/or treating inflammation-related diseases, such as inflammatory bowel diseases (such as ulcerative enteritis, gastritis, and general enteritis) and cardiovascular diseases.

10 Claims, 3 Drawing Sheets

Specification includes a Sequence Listing.

(51) Int. Cl.
    *A61K 35/00*      (2006.01)
    *C12R 1/01*       (2006.01)

(56) References Cited

OTHER PUBLICATIONS

"Uncultured bacterium clone SJTU_D_01_72 16S ribosomal RNA gene, partial sequence," Database EMBL, Accession No. EF400804, retrieved from internet: <https://www.ncbi.nlm.nih.gov/nuccore/ef400804>, 2008.
"Uncultured bacterium clone SJTU_D_04_84 16S ribosomal RNA gene, partial sequence," Database EMBL, Accession No. EF400970, retrieved from internet: <https://www.ncbi.nlm.nih.gov/nuccore/ef400970>, 2008.
"Uncultured bacterium clone SJTU_D_02_33 16S ribosomal RNA gene, partial sequence," Database EMBL, Accession No. EF400848, retrieved from internet: <https://www.ncbi.nlm.nih.gov/nuccore/ef400848>, 2008.
"*Megamonas* sp. Marseille- P3344 partial 16S rRNA gene, strain Marseille-P3344," Database EMBL, Accession No. LT628480, retrieved from internet: <https://www.ncbi.nlm.nih.gov/nuccore/lt628480>, 2016.
JPO, Office Action for JP Application No. 2020-515131, dated Apr. 6, 2021.
EPO, Extended European Search Report for EP Application No. 17925337.2, dated Apr. 1, 2021.
WIPO, ISR for PCT/CN2017/101915, dated Jun. 20, 2018.

\* cited by examiner

SEQUENCE LISTING

<160> NUMBER OF SEQ ID NOS: 3

<210> SEQ ID NO 1
<211> LENGTH: 1423
<212> TYPE: DNA
<213> ORGANISM: Megamonas funiformis

<400> SEQUENCE: 1

| | | | | | | |
|---|---|---|---|---|---|---|
| ttaacacatg | caagtcgaac | ggggtgttta | tttcggtaaa | caccaagtgg | cgaacgggtg | 60 |
| agtaacgcgt | aagcaatcta | ccttcaagat | ggggacaaca | cttcgaaagg | ggtgctaata | 120 |
| ccgaatgaat | gtaagagtat | cgcatgagac | acttactaaa | ggaggcctct | gaaaatgctt | 180 |
| ccgcttgaag | atgagcttgc | gtctgattag | ctagttggtg | agggtaaagg | cccaccaagg | 240 |
| cgacgatcag | tagccggtct | gagaggatga | acggccacat | tgggactgag | acacggccca | 300 |
| gactcctacg | ggaggcagca | gtggggaatc | ttccgcaatg | ggcgaaagcc | tgacggagca | 360 |
| acgccgcgtg | aacgatgaag | gtcttaggat | cgtaaagttc | tgttgttagg | acgaagggt | 420 |
| aagaataata | atacggtttt | tatttgacgg | tacctaacga | ggaagccacg | gctaactacg | 480 |
| tgccagcagc | cgcggtaata | cgtaggcggc | aagcgttgtc | cggaattatt | gggcgtaaag | 540 |
| ggagcgcagg | cgggaaacta | agcggatctt | aaaagtgcgg | ggctcaaccc | cgtgatgggg | 600 |
| tccgaactgg | ttttcttgag | tgcaggagag | gaaagcggaa | ttcccagtgt | agcggtgaaa | 660 |
| tgcgtagata | ttgggaagaa | caccagtggc | gaaggcggct | ttctggactg | taactgacgc | 720 |
| tgaggctcga | aagctagggt | agcgaacggg | attagatacc | ccgtagtcc | tagccgtaaa | 780 |
| cgatggatac | taggtgtggg | aggtatcgac | cccttccgtg | ccggagttaa | cgcaataagt | 840 |
| atcccgcctg | gggagtacgg | ccgcaaggtt | gaaactcaaa | ggaattgacg | ggggcccgca | 900 |
| caagcggtgg | agtatgtggt | ttaattcgac | gcaacgcgaa | gaaccttacc | aagacttgac | 960 |
| attgattgaa | aggcctagag | ataggtccct | tctcttcgga | gaacaagaaa | acaggtggtg | 1020 |
| catggctgtc | gtcagctcgt | gtcgtgagat | gttgggttaa | gtcccgcaac | gagcgcaacc | 1080 |
| cctatactat | gttgccagca | ttacggatgg | gaactcatag | tagactgccg | cggacaacgc | 1140 |
| ggaggaaggc | ggggatgacg | tcaagtcatc | atgcccctta | cgtcttgggc | tacacacgta | 1200 |
| ctacaatggg | atgaacagag | ggaagcgaaa | tcgcgaggtg | gagcggatcc | ctaaaagcat | 1260 |
| ctctcagttc | ggattgtagg | ctgaaactcg | cctacatgaa | gtcggaatcg | ctagtaatcg | 1320 |
| caggtcagca | tactgcggtg | aatacgttcc | cgggccttgt | acacaccgcc | cgtcacacca | 1380 |
| cgaaagtcat | tcacacccga | agccggctaa | gggcctatgg | tac | | 1423 |

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
agagtttgat catggctcag                                               20

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3

```
tagggttacc ttgttacgac tt                                    22
```

MEGAMONAS FUNIFORMIS AND APPLICATIONS THEREOF

CROSS-REFERENCE TO RELATED APPLICATION

This application is a U.S. national phase application of International Application No. PCT/CN2017/101915, filed Sep. 15, 2017, the entire disclosure of which is incorporated herein by reference.

FIELD

This present disclosure relates to the field of microorganism, in particular to *Megamonas funiformis* and applications thereof.

BACKGROUND

Inflammatory bowel disease (IBD) is a type of chronic inflammatory bowel diseases with unknown etiology, which tends to be recurrent, thus seriously affecting the life quality of patients. Modern medicine believes that the inflammatory bowel disease (IBD) is caused by factors including heredity, diet, infection, autoimmunity, psychological factors, environment and the like. Inflammatory bowel disease includes ulcerative colitis (UC) and Crohn's disease (CD), both of which are inflammation-related diseases.

Cardiovascular diseases are the number one killer in developed countries and is increasingly common in developing countries. In recent years, the economy in our country has developed rapidly, living standards of people have improved significantly, and lifestyles are undergoing profound changes. The pace of work and life is quicker, dietary calories are increased but physical activity is reduced. Such unhealthy lifestyles result in significantly increased risk factors for cardiovascular diseases such as obesity and the like, with rapidly increased incidence of cardio-cerebral vascular diseases. Modern medical research believes that the basis of cardio-cerebral vascular diseases is atherosclerosis, of which oxidized low-density lipoprotein (Ox-LDL) is the core of atherosclerosis. At present, domestic patents for preventing cardio-cerebral vascular diseases mainly focus on aspects of promoting blood circulation, reducing stasis, lowering blood lipids or cholesterol, thus lowering low-density lipoprotein (LDL). The prevention of cardio-cerebral vascular diseases in western countries mainly focuses on aspects of lowering blood lipids or cholesterol via anti-oxidation, therefore lots of antioxidant health-care products are used to prevent cardio-cerebral vascular diseases in western countries, however, they do not achieve significant effects. Similarly, application of traditional Chinese medicines for promoting blood circulation and reducing stasis or traditional Chinese health-care medicines for nourishing qi and activating blood circulation to prevent cardio-cerebral vascular diseases in our country just achieves limited efficacy even though effective.

Ulcerative colitis (UC) is an important type of inflammatory bowel disease (IBD) with unknown etiology, which belongs to a type of chronic bowel diseases and of which the lesion parts are mainly in the submucosa of colonic mucosa. Based on current researches, the main causes of ulcerative colitis are host genetic susceptibility, intestinal flora and intestinal mucosal immune response. The clinical and pathological manifestations of ulcerative colitis are constant abdominal pain, diarrhea, mucous and bloody stools as well as recurrent attacks. The number of UC patients in our country has showed significant upward trend recently.

Currently, the clinical medicines for ulcerative colitis (UC) mainly include salicylic acids, adrenal glucocorticoids and immune agents. Salicylic acid drugs are capable of effectively inhibiting prostaglandin synthesis and scavenging oxygen free radicals, so as to achieve the purpose of alleviating inflammatory response, however they can only alleviate inflammation in a short time period and cannot cure the UC disease. For the clinical treatment of ulcerative colitis (UC), the commonly used western medicine of salicylic acids is sulfasalazine (SASP), mainly directing to mild, moderate and chronic UC patients. Adrenal glucocorticoids are preferred for severe or paroxysmal UC patients, such as betamethasone. Immune agents, such as cyclosporine, can affect the progress of immune response by inhibiting the generation of T cell IL-2, thereby inhibiting ulcerative colitis (UC).

The three types of existing drugs for ulcerative colitis (UC) can all alleviate UC to some extent, but they also cause certain side effects. Salicylic acids have side effects of generating gastrointestinal reactions, headache, increased reticulocytes, sperm reduction, rash caused by allergic reaction, liver toxicity, leukopenia, anemia and the like, as well as easily caused bacterial flora disorders and enhanced drug resistance due to antibacterial effects of such drugs. Adrenal glucocorticoids can cause side effects such as metabolic disorders, retention of water and the like, which can only be used as emergency medicines and cannot be administered for a long period. Immune agent therapy is highly drug-dependent and has a long treatment cycle, which is likely to cause nephrotoxicity and secondary infection, thus can only be used as an adjuvant therapy.

Therefore, there is an urgent need in the art to develop a new, non-toxic and non-side effect medicament for treating and/or preventing inflammation-related diseases and cardiovascular diseases.

SUMMARY

The object of the present disclosure is to provide a new, non-toxic and non-side effect medicament for treating and/or preventing inflammation-related diseases and cardiovascular diseases.

In a first aspect, the present disclosure in embodiments provides a strain *Megamonas funiformis*, wherein the strain *Megamonas funiformis* is *Megamonas funiformis*.

In another preferred embodiment, the *Megamonas funiformis* has a sequence of 16s rDNA as shown in SEQ ID NO.:1.

In another preferred embodiment, the *Megamonas funiformis* is *Megamonas funiformis* AF24-28AC with a deposit number of GDMCC 60093.

In another preferred embodiment, the *Megamonas funiformis* is derived from intestine, animal faeces, a fermentation tank and/or an anaerobic reactor.

In another preferred embodiment, the *Megamonas funiformis* is derived from human or non-human mammals.

In another preferred embodiment, the non-human mammal includes rodents such as mice and rats, and primates such as monkeys.

In a second aspect, the present disclosure in embodiments provides a composition comprising (a) a safe and effective amount of *Megamonas funiformis* of the first aspect of the present disclosure and/or metabolites thereof and (b) a food acceptable or pharmaceutically acceptable carrier.

In another preferred embodiment, the composition further contains a growth factor, preferably a milk growth factor.

In another preferred embodiment, the composition is selected from the group consisting of a food composition, a health care composition, a pharmaceutical composition, a beverage composition, a feed composition or a combination thereof.

In another preferred embodiment, the composition is an oral preparation.

In another preferred embodiment, the composition is a liquid preparation, a solid preparation or a semi-solid preparation.

In another preferred embodiment, the dosage form of the composition is selected from the group consisting of powder, pulvis, tablet, sugar coating agent, capsule, granule, suspension, solution, syrup, drop, sublingual tablet or a combination thereof.

In another preferred embodiment, the food composition includes an emulsion product, a solution product, a powder product or a suspension product.

In another preferred embodiment, the food composition includes dairy, milk powder or emulsion.

In another preferred embodiment, the liquid preparation is selected from the group consisting of a solution product or a suspension product.

In another preferred embodiment, the composition contains $1\times10$-$1\times10^{15}$ cfu/mL or cfu/g of *Megamonas funiformis* AF24-28AC, preferably $1\times10^{4}$-$1\times10^{10}$ cfu/mL or cfu/g of *Megamonas funiformis* AF24-28AC, based on the total volume or total weight of the composition.

In another preferred embodiment, the composition contains 0.0001 wt % to 99 wt %, preferably 0.1 wt % to 90 wt % of *Megamonas funiformis* and/or metabolites thereof, based on the total weight of the composition.

In another preferred embodiment, the composition is in a unit dosage form, i.e., one tablet, one capsule or one vial, and the composition in each unit dosage form is of a mass of 0.05 g to 5 g, preferably 0.1 g to 1 g.

In another preferred embodiment, the composition further contains probiotics and/or prebiotics.

In another preferred embodiment, the probiotics are selected from the group consisting of Lactic acid bacteria, *Bifidobacteria, Lactobacillus acidophilus* or a combination thereof.

In another preferred embodiment, the prebiotics are selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof.

In another preferred embodiment, the composition further contains a substance capable of maintaining the viability of *Megamonas funiformis*, such as a protective agent.

In another preferred embodiment, the substance capable of maintaining the viability of *Megamonas funiformis* such as a protective agent is selected from the group consisting of cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E or a combination thereof.

In another preferred embodiment, the substance capable of maintaining the viability of *Megamonas funiformis* such as a protective agent is of a weight ratio of 0.1% to 2%, preferably 0.5% to 1.5%, more preferably 0.5% to 1.0%, based on the total weight of the composition.

In another preferred embodiment, the substance capable of maintaining the viability of *Megamonas funiformis* such as a protective agent is of an amount of 1 mg to 20 mg, preferably 5 mg to 15 mg, more preferably 5 mg to 10 mg, based on 1 g of the composition.

In a third aspect, the present disclosure in embodiments provides use of the *Megamonas funiformis* of the first aspect of the present disclosure or the composition of the second aspect of the present disclosure in the manufacture of a composition or a preparation for one or more selected from the group consisting of:

(a) preventing and/or treating inflammation-related diseases; and/or (b) preventing and/or treating cardiovascular diseases.

In another preferred embodiment, the inflammation-related diseases are selected from the group consisting of inflammatory bowel disease, rheumatoid arthritis or a combination thereof.

In another preferred embodiment, the inflammation-related diseases are selected from the group consisting of ulcerative colitis, gastritis, general enteritis or a combination thereof.

In another preferred embodiment, the cardiovascular diseases are selected from the group consisting of hypertension, hyperlipidemia, coronary heart disease or a combination thereof.

In another preferred embodiment, the preparation includes a microecological preparation.

In a fourth aspect, the present disclosure in embodiments provides use of the *Megamonas funiformis* of the first aspect of the present disclosure or the composition of the second aspect of the present disclosure in the manufacture of a composition or a preparation for one or more selected from the group consisting of:

(i) lowering blood lipid levels in a mammal;
(ii) controlling weight loss in a mammal;
(iii) decreasing disease activity index (DAI) in a mammal; and
(iv) relieving intestinal lesions in a mammal.

In another preferred embodiment, the lowering blood lipid levels in a mammal includes lowering cholesterol level.

In another preferred embodiment, the controlling weight loss in a mammal refers to the body weight of a mammal in an experimental group is reduced by not more than 10%, preferably not more than 5%, more preferably not more than 2% compared to a mammal in a model group.

In another preferred embodiment, the relieving intestinal lesions in a mammal includes slowing the shortening of colon length and/or alleviating the inflammation reaction of colon.

In another preferred embodiment, the mammal includes human or non-human mammals.

In another preferred embodiment, the non-human mammal includes rodents such as mice and rats, and primates such as monkeys.

In a fifth aspect, the present disclosure in embodiments provides a method for preparing the composition of the second aspect of the present disclosure, comprising a step of:

mixing the *Megamonas funiformis* of the first aspect of the present disclosure and/or metabolites thereof with a food acceptable or pharmaceutically acceptable carrier to form the composition of the second aspect of the present disclosure.

In another preferred embodiment, the method further includes a step of mixing with a growth factor.

In another preferred embodiment, the method further includes a step of mixing with a substance capable of maintaining the viability of *Megamonas funiformis*, such as a protective agent.

In another preferred embodiment, the substance capable of maintaining the viability of *Megamonas funiformis* such as a protective agent is selected from the group consisting of cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E or a combination thereof.

In another preferred embodiment, the method further includes a step of mixing with probiotics and/or prebiotics.

In another preferred embodiment, the probiotics are selected from the group consisting of Lactic acid bacteria, *Bifidobacteria, Lactobacillus acidophilus* or a combination thereof.

In another preferred embodiment, the prebiotics are selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof.

In another preferred embodiment, the growth factor is a milk growth factor.

In another preferred embodiment, the growth factor is selected from the group consisting of vitamins, purines, pyrimidines or a combination thereof.

In another preferred embodiment, the composition is an oral preparation.

In a sixth aspect, the present disclosure in embodiments provides a production method, comprising steps of:

(a) culturing the *Megamonas funiformis* of the first aspect of the present disclosure under a condition suitable for culturing, thereby obtaining a culture product;

(b) optionally, isolating *Megamonas funiformis* bacteria cells and/or metabolites thereof from the culture product; and/or (c) optionally, mixing the culture product obtained in (a) or the *Megamonas funiformis* bacteria cells and/or metabolites thereof obtained in (b) with a food acceptable or pharmaceutically acceptable carrier, thereby obtaining a composition of the present disclosure.

In another preferred embodiment, prior to step (c), the method further includes a step of mixing the culture product obtained in (a) or the *Megamonas funiformis* bacteria cells and/or metabolites thereof obtained in (b) with a growth factor.

In another preferred embodiment, the growth factor is a milk growth factor.

In another preferred embodiment, the growth factor is selected from the group consisting of vitamins, purines, pyrimidines or a combination thereof.

In another preferred embodiment, prior to step (c), the method further includes a step of mixing the culture product obtained in (a) or the *Megamonas funiformis* bacteria cells and/or metabolites thereof obtained in (b) with a substance capable of maintaining the viability of *Megamonas funiformis* such as a protective agent.

In another preferred embodiment, prior to step (c), the method further includes a step of mixing the culture product obtained in (a) or the *Megamonas funiformis* bacteria cells and/or metabolites thereof obtained in (b) with probiotics and/or prebiotics.

In a seventh aspect, the present disclosure in embodiments provides a method for relieving intestinal lesions in a mammal, comprising administering the composition of the second aspect of the present disclosure to the mammal.

In another preferred embodiment, the composition is administered orally.

In another preferred embodiment, the administration dosage is 0.01 to 5 g/50 kg body weight per day, preferably 0.1 to 2 g/50 kg body weight per day.

In another preferred embodiment, the mammal includes human or non-human mammal.

In another preferred embodiment, the non-human mammal includes rodents such as mice and rats, and primates such as monkeys.

In another preferred embodiment, the method is non-therapeutic or non-diagnostic.

In an eighth aspect, the present disclosure in embodiments provides a method for lowering blood lipid levels, controlling weight loss and/or decreasing disease activity index (DAI) in a mammal, comprising administering the composition of the second aspect of the present disclosure to the mammal.

In another preferred embodiment, the composition is administered orally.

In another preferred embodiment, the administration dosage is 0.01 to 5 g/50 kg body weight per day, preferably 0.1 to 2 g/50 kg body weight per day.

In another preferred embodiment, the mammal includes human or non-human mammals.

In another preferred embodiment, the non-human mammal includes rodents such as mice and rats, and primates such as monkeys.

In another preferred embodiment, the method is non-therapeutic or non-diagnostic.

In a ninth aspect, the present disclosure in embodiments provides a method for preventing and/or treating inflammation-related diseases, comprising a step of:

administering the composition of the second aspect of the present disclosure to a subject, thereby preventing and/or treating inflammation-related diseases.

In another preferred embodiment, the composition is administered orally.

In another preferred embodiment, the administration dosage is 0.01 to 5 g/50 kg body weight per day, preferably 0.1 to 2 g/50 kg body weight per day.

In another preferred embodiment, the subject includes human or non-human mammal.

In another preferred embodiment, the non-human mammal includes rodents such as mice and rats, and primates such as monkeys.

In another preferred embodiment, the method is non-therapeutic or non-diagnostic.

In a tenth aspect, the present disclosure in embodiments provides a method for preventing and/or treating cardiovascular diseases, comprising a step of:

administering the composition of the second aspect of the present disclosure to a subject, thereby preventing and/or treating cardiovascular diseases.

In another preferred embodiment, the composition is administered orally.

In another preferred embodiment, the administration dosage is 0.01 to 5 g/50 kg body weight per day, preferably 0.1 to 2 g/50 kg body weight per day.

In another preferred embodiment, the subject includes human or non-human mammals.

In another preferred embodiment, the non-human mammal includes rodents such as mice and rats, and primates such as monkeys.

In another preferred embodiment, the method is non-therapeutic or non-diagnostic.

It should be understood that, the technical features of the present disclosure as described above and the technical features as specifically described below (such as examples)

DETAILED DESCRIPTION

Figure 1:
FIG. 1 is a picture showing colony of *Megamonas funiformis* AF24-28AC after culturing for 48 hours.

Present inventors have surprisingly discovered that strain *Megamonas funiformis* exhibits the efficacy of preventing and/or treating inflammation-related diseases (for example, inflammatory bowel disease (such as ulcerative colitis, gastritis and general enteritis) and rheumatoid arthritis) and/or cardiovascular diseases (such as hypertension, hyperlipidemia, coronary heart disease), after extensive and intensive researches and experiments. It is found that the active composition containing *Megamonas funiformis* of the present disclosure is capable of controlling weight loss, lowering blood lipids, decreasing disease activity index (DAI) and relieving intestinal lesions, thus can effectively alleviate inflammation-related diseases (for example, inflammatory bowel disease (such as ulcerative colitis, gastritis and general enteritis) and rheumatoid arthritis), cardiovascular diseases and the like through feeding experimental subjects. On this basis, the present inventors have completed the present disclosure.

As used herein, the term "comprising" means that various components can be applied together in a mixture or a composition of the present disclosure. Accordingly, the terms "essentially consisting of . . . " and "consisting of . . . " are included in the scope of the term "comprising".

As used herein, the term "growth factor" includes a milk growth factor, specifically including nutrients of vitamins, purines, pyrimidines or a combination thereof.

In which, the vitamins include but are not limited to Vitamin C, Vitamin E, Vitamin A, Vitamin A precursor, Vitamin B6, Vitamin D3, Vitamin K, folic acid or a combination thereof;

the purines include but are not limited to purine nucleosides, which include 5'-phosphate esters of purine nucleosides; the 5'-phosphate esters of purine nucleosides are selected from the group consisting of inosinic acid (inosine-5'-phosphate ester; IMP), guanylic acid (guanosine-5'-phosphate ester; GMP), xanthylic acid (xanthine-5'-phosphate ester; XMP), adenylic acid (adenosine-5'-phosphate ester; AMP) or a combination thereof;

the pyrimidines include all substances containing a pyrimidine structure.

As used herein, the terms "controlling weight loss in a mammal", "slowing weight loss in a mammal", "controlling weight decrease in a mammal" and "slowing weight decrease in a mammal" can be used interchangeably and refer to the body weight of experimental animals is decreased during the construction of ulcerative colitis model due to the increasing severity of inflammation, and the weight loss percentage is the percentage of decreased body weight to original body weight. The higher the body weight decreases, the more serious the disease is. During the treatment of ulcerative colitis in a mammal, the *Megamonas funiformis* of the present disclosure can control the weight loss of experimental animals and alleviate the symptoms of disease.

Disease Activity Index (DAI)

As used herein, the term "disease activity index" refers to a comprehensive score of three indicators (i.e., the weight loss percentage, stool viscosity and stool bleeding) in a patient or an affected animal.

*Megamonas funiformis* and Application Thereof

As used herein, the terms "strain *Megamonas funiformis*", "*Megamonas funiformis*" and "*Megamonas funiformis* of the present disclosure" can be used interchangeably. In a preferred embodiment, the strain is *Megamonas funiformis* AF24-28AC with a deposit number of GDMCC 60093, which is isolated from human feces, preferably a healthy female. The physiological characteristics of *Megamonas funiformis* is described as follows. The *Megamonas funiformis* AF24-28AC is isolated by using PYG medium in an anaerobic condition at 37° C. The colony of *Megamonas funiformis* AF24-28AC after culturing for 2 days in PYG medium is light yellow, flat, with irregular wavy edges and low water content, and about 2-3 mm in diameter. The mycelium under microscope is rod-shaped, Gram-negative, and does not produce spores and flagella. *Megamonas funiformis* AF24-28AC is detected to be negative to catalase and oxidase. *Megamonas funiformis* AF24-28AC can produce several carbohydrates after fermentation, including glucose, mannitol, lactose, sucrose, maltose, salicyl alcohol, xylose, arabinose, glycerol, cellobiose, mannitol, melezitose, raffinose, sorbitol, rhamnose and trehalose; can mainly produce acetic acid, propionic acid, isovaleric acid, benzoic acid and lactic acid; and can also produce a small amount of valeric acid, 3-methyl butyric acid, maleic acid, succinic acid, malic acid, adipic acid and citric acid. Moreover, the *Megamonas funiformis* AF24-28AC of the present disclosure is resistant to penicillin, oxacillin and cefoperazone, while it is sensitive to other 17 antibiotics in Table 2.

The present disclosure provides use of *Megamonas funiformis* in preventing and/or treating inflammation-related diseases (for example, inflammatory bowel disease (such as ulcerative colitis, gastritis, general enteritis), rheumatoid arthritis) and cardiovascular diseases (such as hypertension, hyperlipidemia, coronary heart disease). Dextran sodium sulfate (DSS) is used to induce a model in a subject. The strain *Megamonas funiformis* AF24-28AC is capable of one or more selected from the group consisting of (i) controlling weight loss in a subject, (ii) decreasing disease activity index (DAI), (iii) relieving intestinal lesions, and (iv) lowering blood lipid levels. According to a preferred embodiment of the present disclosure, C57bl/6 mice are used as experimental mice and dextran sodium sulfate (DSS) is used to induce a model, thus obtaining the ulcerative colitis (UC) mouse model, which is then treated with *Megamonas funiformis* AF24-28AC. The *Megamonas funiformis* AF24-28AC-treated UC mouse model exhibits slowed weight loss, decreased blood lipids, and alleviated indicators associated with inflammation-related diseases (for example, inflammatory bowel disease (such as ulcerative colitis, gastritis, general enteritis), rheumatoid arthritis), such as relieving intestinal lesions (including slowing the shortening of colon length, reducing the inflammation reaction in colon and the like), decreasing disease activity index (DAI) and the like, compared to the untreated control group (a model group).

Therefore, the strain can be useful in preventing and/or treating inflammation-related diseases (such as inflammatory bowel diseases (such as ulcerative colitis, gastritis, general enteritis), rheumatoid arthritis), cardiovascular diseases (such as hypertension, hyperlipidemia, coronary heart disease).

Composition and Application Thereof

The present disclosure also provides a composition. Preferably, the composition includes a food composition, a health care composition, a pharmaceutical composition, a beverage composition or a feed composition. More preferably, the composition is a pharmaceutical composition. The composition contains an effective amount of *Megamonas funiformis*. In a preferred embodiment, the composition further contains a growth factor, such as a milk growth factor. In a preferred embodiment, the composition further contains probiotics selected from the group consisting of Lactic acid bacteria, *Bifidobacteria, Lactobacillus acidophilus* or a combination thereof; and/or prebiotics selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof. In a preferred embodiment, the composition further contains a substance capable of maintaining the viability of *Megamonas funiformis* (such as a protective agent), which includes cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E or a combination thereof. The substance capable of maintaining the viability of *Megamonas funiformis* (such as a protective agent) is of a weight ratio of 0.1% to 2%, preferably 0.5% to 1.5%, more preferably 0.5% to 1.0%, based on the total weight of the composition.

In a preferred embodiment, the composition is a liquid preparation, a solid preparation or a semi-solid preparation.

In a preferred embodiment, the liquid preparation is selected from the group consisting of a solution product or a suspension product.

In a preferred embodiment, the dosage form of the composition is selected from the group consisting of powder, pulvis, tablet, sugar coating agent, capsule, granule, suspension, solution, syrup, drop, sublingual tablet or a combination thereof.

The composition of the present disclosure may be administered in any form of oral solution, tablet, injection, orally disintegrating tablet, lyophilized powder or capsule, preferably in the dosage form of enteric agent (such as capsule). In the present disclosure, the excipient, pharmaceutically acceptable vehicle and carrier used in the present disclosure are mainly selected depending on the property suitable for the bacteria or metabolites thereof and the specific administration means required, which is beneficial to the smooth passage of the bacteria or metabolites thereof through stomach thus absorbed by the administered subject, without special indication. These substances can be selected according to the administration route.

The composition of the present disclosure may further contain any additional excipients among those commonly used in pharmaceutical preparations, for example, for stabilization of the composition itself, or allowing to be easily dispersed or imparting a suitable taste.

Among the excipients, suitable examples are inulin, fructose, starch, xylooligosaccharide, silicon dioxide, buffering agent and flavoring agent.

The pharmaceutical preparation of the present disclosure may further contain an auxiliary active component.

Lactose, maltodextrin, glucose, sucrose, sorbitol, mannose, starch, arabic gum, calcium phosphate, alginate, gelatin, calcium silicate, fine crystalline cellulose, polyvinylpyrrolidone (PVP), cellulose, water, syrup, methyl cellulose, methyl hydroxybenzoate, propyl hydroxybenzoate, talc, magnesium stearate, mineral oil and the like can be all used as carriers, excipients, diluents and the like of the pharmaceutical composition of the present disclosure.

Further, the pharmaceutical composition of the present disclosure may further contain lubricant, wetting agent, emulsifier, suspension stabilizer, preservative, sweetening agent, flavor and the like. The pharmaceutical composition of the present disclosure can be produced in an enteric coating preparation via a variety of well-known methods, so that the active component of the pharmaceutical composition (i.e., the microorganism) can pass through stomach smoothly without destroyed by gastric acid.

Further, the microorganism of the present disclosure may be used in the form of capsule prepared by conventional methods. For example, standard excipients and lyophilized microorganism of the present disclosure are mixed to obtain pills which are subsequently dispensed into gelatin capsules. In addition, the microorganism of the present disclosure and pharmaceutically acceptable excipients (such as liquid gum, cellulose, silicate, mineral oil and the like) can be mixed and prepared in suspension or dispersion, and such a suspension or dispersion can be filled into soft gelatin capsules.

The pharmaceutical composition of the present disclosure can be prepared in enteric coating tablets for oral use. The term "enteric coating" in the present disclosure includes all coatings that are allowed for conventional drugs. These coatings are not degraded by gastric acid, however, can be completely broken down in small intestine and then quickly release the microorganism of the present disclosure. The enteric coating of the present disclosure can be maintained in a HCl solution for gastric acid synthesis (such as pH=1) at 36° C. to 38° C. for more than 2 hours, preferably broken down in a buffer solution for intestinal fluid synthesis (such as pH=7.0) within one hour.

The enteric coating of the present disclosure is coated in an amount of about 16 to 30 mg per tablet, preferably 16 to 25 mg per tablet, and more preferably 16 to 20 mg per tablet. The thickness of the enteric coating in the present disclosure is 5 to 100 μm, ideally 20 to 80 μm. The components of enteric coating are selected from conventional polymers which are known in public.

The preferred enteric coating of the present disclosure is prepared by a copolymer of cellulose acetate phthalate polymer or cellulose acetate trimellitate polymer and methacrylic acid, for example, a copolymer of methacrylic acid and methylcellulose hydroxypropyl phthalate or its ester derivatives, in which the amount of methacrylic acid is more than 40%.

The cellulose acetate phthalate used in the enteric coating of the present disclosure has a viscosity of about 45 to 90 cp, an acetyl content of 17 to 26%, and a phthalic acid content of 30 to 40%. The cellulose acetate trimellitate used in the enteric coating has a viscosity of about 5 to 21 cp, and an acetyl content of 17 to 26%. Cellulose acetate trimellitate, produced by Eastman Kodak Company, can be used as the enteric coating material in the present disclosure.

The hydroxypropyl methylcellulose phthalate used in the enteric coating of the present disclosure generally has a molecular weight of 20,000 to 130,000 Daltons (ideally 80,000 to 100,000 Daltons), a hydroxypropyl content of 5 to 10%, a methoxyl content of 18 to 24% and a phthaloyl content of 21 to 35%.

The hydroxypropyl methylcellulose phthalate used in the enteric coating of the present disclosure is HP50, produced by Shin-Etsu Chemical Co. Ltd. of Japan. HP50 contains 6 to 10% of hydroxypropyl, 20 to 24% of methoxy and 21 to 27% of propyl, with a molecular weight of 84,000 Daltons. Another enteric coating material is HP55, which contains 5 to 9% of hydroxypropyl, 18 to 22% of methoxy and 27 to 35% of phthalic acid, with a molecular weight of 78,000 Daltons.

The enteric coating of the present disclosure is prepared by spraying the enteric coating solution onto the core through conventional methods. Solvents for the enteric coating are alcohols (such as ethanol), ketones (such as acetone), halogenated hydrocarbon compounds (such as dichloromethane) or a combination thereof. Softeners such as di-n-butyl phthalate and glyceryl triacetate are added to the enteric coating solution in a ratio of 1 part of the coating to about 0.05 parts (or about 0.3 parts) of the softener. The spraying method is preferably performed continuously, and the amount of spray material can be controlled according to the conditions for coating. The spray pressure can be adjusted flexibly, generally, an average pressure of 1 to 1.5 Pa will result in ideal results.

The "pharmaceutically effective amount" in the specification refers to an amount which is functional or active to human and/or animals and is acceptable to human and/or animals. For example, a preparation containing $1\times10$-$1\times10^{15}$ cfu/ml or cfu/g (particularly $1\times10^4$-$1\times10^{10}$ cfu/ml or cfu/g, more particularly $1\times10^6$-$1\times10^{10}$ cfu/ml or cfu/g) of *Megamonas funiformis* and/or metabolites thereof can be prepared in the present disclosure.

When the *Megamonas funiformis* is used in the manufacture of a pharmaceutical composition, the effective dosage of *Megamonas funiformis* or metabolites thereof used may vary depending on the administration route and the severity of disease to be treated. A dosage form suitable for internal administration includes about $1\times10$-$1\times10^{15}$ cfu/ml or cfu/g (particularly $1\times10^4$-$1\times10^{10}$ cfu/ml or cfu/g, more particularly $1\times10^6$-$1\times10^{10}$ cfu/ml or cfu/g) of active *Megamonas funiformis* or its active component produced by fermentation, which is closely mixed with a solid or liquid pharmaceutically acceptable carrier. This dosage regimen can be adjusted to provide the best therapeutic response. For example, several divided doses may be administered daily, or the dosage may be proportionally reduced according to the urgent need of treatment condition.

The *Megamonas funiformis* or metabolites thereof may be administered by oral route and the like. Solid carriers include starch, lactose, dicalcium phosphate, microcrystalline cellulose, sucrose and white clay; and liquid carriers include culture medium, polyethylene glycol, non-ionic surfactants and edible oils (such as corn oil, peanut oil and sesame oil), as long as they are suitable for the property of *Megamonas funiformis* or metabolites thereof and the specific administration means required. Adjuvants commonly used in the manufacture of pharmaceutical composition may also be advantageously included, for example, flavoring agents, pigments, preservatives and antioxidants such as Vitamin E, Vitamin C, BHT and BHA.

From the standpoint of ease of manufacture and administration, preferred pharmaceutical composition is the solid composition, especially tablets and/or solid-filled or liquid-filled capsules. Preferred is oral administration.

The composition of the present disclosure is administered to individuals once or several times per day. The dosage unit of administration refers to a dosage that is physically separated and suitable for application in human or all individuals of other mammals. Each unit contains a pharmaceutically acceptable carrier and a therapeutically effective amount of microorganism of the present disclosure. The administration dosage varies with the body weight and severity of inflammation-related diseases (for example, inflammatory bowel disease (such as ulcerative colitis, gastritis, general enteritis), rheumatoid arthritis) and cardiovascular diseases in a patient, the contained supplementary active components and the microorganism used. Further, if possible, the composition can be administered separately and continuously as necessary. Therefore, the administration dosage does not limit the scope of the present disclosure. In addition, the "composition" in the present disclosure means not only a medicament but also a functional food and a health supplement food. In a preferred embodiment, the composition includes beverage, food, medicine, animal feed and the like.

In a preferred embodiment, the present disclosure further provides a food composition, which contains an effective amount of *Megamonas funiformis* and/or metabolites thereof as well as a food acceptable carrier as balance. The dosage form of the food composition is selected from a solid product, a dairy product, a solution product, a powder product or a suspension product. In a preferred embodiment, the food composition may further contain a growth factor, such as a milk growth factor. In a preferred embodiment, the composition further contains probiotics selected from the group consisting of Lactic acid bacteria, *Bifidobacteria*, *Lactobacillus acidophilus* or a combination thereof; and/or prebiotics selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof. In a preferred embodiment, the composition further contains a substance capable of maintaining the viability of *Megamonas funiformis* (such as a protective agent), including cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E or a combination thereof.

In a preferred embodiment, the composition has the following formula:

$1\times10$-$1\times10^{15}$ cfu/mL of *Megamonas funiformis* and/or metabolites thereof, and a food or pharmaceutically acceptable carrier and/or excipient.

In another preferred embodiment, the composition has the following formula:

$1\times10^4$-$1\times10^{10}$ cfu/mL of *Megamonas funiformis* and/or metabolites thereof; and a food or pharmaceutically acceptable carrier and/or excipient.

Microecological Preparation

Microecological preparation is a biological preparation containing probiotics and metabolites thereof or a dietary supplement that can supply probiotics, which are capable of adjusting and maintaining the microecological balance in intestine, thus achieving the purpose of improving human health. The microecological preparation mainly includes probiotics, prebiotics and synbiotics.

In the present disclosure, the microecological preparation contains (a) a safe and effective amount of *Megamonas funiformis* and/or metabolites thereof, and (b) a food acceptable or pharmaceutically acceptable carrier. In a preferred embodiment, the preparation further contains a growth factor, such as a milk growth factor, preferably including vitamins, purines and/or pyrimidines. In a preferred embodiment, the preparation further contains probiotics selected from the group consisting of Lactic acid bacteria, *Bifidobacteria, Lactobacillus acidophilus* or a combination thereof; and/or prebiotics selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof. In a preferred embodiment, the composition further contains a substance capable of maintaining the viability of *Megamonas funiformis* (such as a protective agent) selected from the group consisting of cysteine, glutathione, butyl hydroxyanisole, dibutylmethyltoluene, tocopherol, antioxidant of bamboo, D-isoascorbic acid and sodium salt thereof, sodium ascorbate, calcium ascorbate, phospholipid, Vitamin C (ascorbic acid), Vitamin E or a combination thereof.

Method for Producing *Megamonas funiformis*

Generally, *Megamonas funiformis* can be produced by conventional methods.

In the present disclosure, provided is a method capable of producing *Megamonas funiformis* on a large scale. In particular, the method includes steps of:

(a) culturing the *Megamonas funiformis* of the present disclosure under a condition suitable for culturing, thereby obtaining a culture product;

(b) optionally, isolating *Megamonas funiformis* bacteria cells and/or metabolites thereof from the culture product; and (c) optionally, mixing the culture product obtained in (a) or the *Megamonas funiformis* bacteria cells and/or metabolites thereof obtained in (b) with a food acceptable or pharmaceutically acceptable carrier, thereby obtaining a composition.

In the present disclosure, the condition suitable for culturing refers to any conditions suitable for culturing *Megamonas funiformis* of the present disclosure. In a preferred embodiment, the condition suitable for culturing refers to anaerobic culturing with PYG medium at 37° C. for 24 to 72 hours.

Method for Relieving Intestinal Lesions in a Mammal

In another preferred embodiment, the method includes ingesting a pharmaceutical composition, a food composition, a beverage composition or a combination thereof of the present disclosure. The experimental subject is a mammal, such as human.

In another preferred embodiment, the method includes ingesting a pharmaceutical composition, a food composition, an animal feed or a combination thereof of the present disclosure. The experimental subjects are animals, preferably mice or rabbits.

Method for Controlling Weight Loss and/or Decreasing Disease Activity Index (DAI) in a Mammal In another preferred embodiment, the method includes ingesting a pharmaceutical composition, a food composition, a beverage composition or a combination thereof of the present disclosure. The experimental subject is a mammal, such as human.

In another preferred embodiment, the method includes ingesting a pharmaceutical composition, a food composition, an animal feed or a combination thereof of the present disclosure. The experimental subjects are animals, preferably mice or rabbits.

Method for Lowering Blood Lipid in a Mammal

In another preferred embodiment, the method includes ingesting a pharmaceutical composition, a food composition, a beverage composition or a combination thereof of the present disclosure. The experimental subject is a mammal, such as human.

In another preferred embodiment, the method includes ingesting a pharmaceutical composition, a food composition, an animal feed or a combination thereof of the present disclosure. The experimental subjects are animals, preferably mice or rabbits.

Method for Preventing and/or Treating Inflammation-Related Diseases

In another preferred embodiment, the method includes ingesting a pharmaceutical composition, a food composition, a beverage composition or a combination thereof of the present disclosure. The experimental subject is a mammal, such as human.

In another preferred embodiment, the method includes ingesting a pharmaceutical composition, a food composition, an animal feed or a combination thereof of the present disclosure. The experimental subjects are animals, preferably mice or rabbits.

Method for Preventing and/or Treating Cardiovascular Diseases

In another preferred embodiment, the method includes ingesting a pharmaceutical composition, a food composition, a beverage composition or a combination thereof of the present disclosure. The experimental subject is a mammal, such as human.

In another preferred embodiment, the method includes ingesting a pharmaceutical composition, a food composition, an animal feed or a combination thereof of the present disclosure. The experimental subjects are animals, preferably mice or rabbits.

Deposit of Microorganism

The strain *Megamonas funiformis* AF24-28AC of the present disclosure was deposited at Guangdong Microbial Culture Collection Center (GDMCC, fifth floor of No. 59 Building, 100 Xianlie Middle Road, Guangzhou) on Oct. 13, 2016, with a deposit number of GDMCC 60093 and a deposit name of *Megamonas funiformis* AF24-28AC.

The advantages of the present disclosure mainly include the followings:

(a)*Megamonas funiformis* of the present disclosure is capable of significantly alleviating indicators associated with inflammation-related diseases (for example, inflammatory bowel disease (such as ulcerative colitis, gastritis, general enteritis), rheumatoid arthritis), for example, controlling weight loss, relieving intestinal lesions (including slowing the shortening of colon length, reducing the inflammation reaction in colon and the like), decreasing disease activity index (DAI) and the like.

(b) *Megamonas funiformis* of the present disclosure is capable of significantly lowering blood lipid levels, such as cholesterol level.

(c)*Megamonas funiformis* AF24-28AC of the present disclosure exhibits the following efficacy on UC mice: effectively controlling weight loss of UC mice induced by DSS, inhibiting the increase of disease activity index (DAI) of mice, relieving intestinal lesions of mice and degrading cholesterol.

The present disclosure is further described below with reference to specific embodiments. It should be understood that these examples are only for illustrating the present disclosure and not intended to limit the scope of the present disclosure. The conditions of experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions described in the Journal of Microbiology: An Experimental Handbook (edited by James Cappuccino and Natalie Sherman, Pearson Education Press) or the manufacturer's proposed conditions.

Unless otherwise specified, the materials and agents used in the examples are all commercially available products.

Example 1: Isolation and Identification of *Megamonas funiformis* AF24-28AC

The sample to be isolated was obtained from faeces of a healthy female, which was subjected to isolation by a spread plate method in gradient dilution. The plates were cultured by PYG medium (purchased from Huankai Microbial Technology Co., Ltd.) in an anaerobic condition (anaerobic gas components: $N_2:CO_2:H_2=90:5:5$) for 48 hours. Single colonies were picked out and purified by streaking to obtain a pure culture of each single colony.

The genomic DNA of isolated bacteria was extracted, followed by PCR amplification using 16S rDNA universal primers 27f and 1492r according to the following amplification condition.

The primer 27f is of a sequence of
(SEQ ID NO.: 2)
5'-AGAGTTTGATCATGGCTCAG-3'.

The primer 1492r is of a sequence of
(SEQ ID NO.: 3)
5'-TAGGGTTACCTTGTTACGACTT-3'.

The amplification condition was as below:

| | | | |
|---|---|---|---|
| 94° C. | 4 mins | | |
| 94° C. | 30 s | } | } 20 cycles |
| 65° C.-57° C. | 40 s | } | |
| 72° C. | 1 min and 30 s | | |
| 94° C. | 30 s | | |
| 57° C. | 40 s | | 10 cycles |
| 72° C. | 1 min and 30 s | | |
| 72° C. | 10 mins | | |
| 4° C. | ∞ | | |

The obtained 16S rDNA amplification product was subjected to electrophoretic detection, purification and 3730 sequencing to obtain a 16S rDNA sequence (SEQ ID NO.:1) with a length of 1423 bp. The 16S rDNA sequence of strain AF24-28AC was subjected to alignment on EzBioCloud database (http://www.ezbiocloud.net/identify). It is found that strain *Megamonas funiformis* (*Megamonas funiformis* DSM 19343, purchased from the Deutsche Sammlung von Mikroorganismen and Zellkulturen, DSMZ) has the highest homology (i.e., 99.09%) with the AF24-28AC. Thus, it can be substantively identified that the AF24-28AC belongs to *Megamonas funiformis*.

(SEQ ID NO.: 1)

```
ttaacacatg caagtcgaac ggggtgttta tttcggtaaa caccaagtgg cgaacgggtg   60
agtaacgcgt aagcaatcta ccttcaagat ggggacaaca cttcgaaagg ggtgctaata  120
ccgaatgaat gtaagagtat cgcatgagac acttactaaa ggaggcctct gaaaatgctt  180
ccgcttgaag atgagcttgc gtctgattag ctagttggtg agggtaaagg cccaccaagg  240
cgacgatcag tagccggtct gagaggatga acggccacat tgggactgag acacggccca  300
gactcctacg ggaggcagca gtggggaatc ttccgcaatg ggcgaaagcc tgacggagca  360
acgccgcgtg aacgatgaag gtcttaggat cgtaaagttc tgttgttagg gacgaagggt  420
aagaataata atacggtttt tatttgacgg tacctaacga ggaagccacg gctaactacg  480
tgccagcagc cgcggtaata cgtaggcggc aagcgttgtc cggaattatt gggcgtaaag  540
ggagcgcagg cgggaaacta agcggatctt aaaagtgcgg ggctcaaccc cgtgatgggg  600
tccgaactgg ttttcttgag tgcaggagag gaaagcggaa ttcccagtgt agcggtgaaa  660
tgcgtagata ttgggaagaa caccagtggc gaaggcggct ttctggactg taactgacgc  720
tgaggctcga aagctagggt agcgaacggg attagatacc ccggtagtcc tagccgtaaa  780
cgatggatac taggtgtggg aggtatcgac cccttccgtg ccggagttaa cgcaataagt  840
atcccgcctg gggagtacgg ccgcaaggtt gaaactcaaa ggaattgacg ggggcccgca  900
caagcggtgg agtatgtggt ttaattcgac gcaacgcgaa gaaccttacc aagacttgac  960
attgattgaa aggcctagag ataggtccct tctcttcgga gaacaagaaa acaggtggtg 1020
catggctgtc gtcagctcgt gtcgtgagat gttgggttaa gtcccgcaac gagcgcaacc 1080
cctatactat gttgccagca ttacgatgg gaactcatag tagactgccg cggacaacgc 1140
ggaggaaggc ggggatgacg tcaagtcatc atgccccctta cgtcttgggc tacacacgta 1200
ctacaatggg atgaacagag ggaagcgaaa tcgcgaggtg gagcggatcc ctaaaagcat 1260
```

```
ctctcagttc ggattgtagg ctgaaactcg cctacatgaa gtcggaatcg ctagtaatcg  1320
caggtcagca tactgcggtg aatacgttcc cgggccttgt acacaccgcc cgtcacacca  1380
cgaaagtcat tcacacccga agccggctaa gggcctatgg tac                    1423
```

1.1 Physiological and Biochemical Characteristics of AF24-28AC

Figure 2:
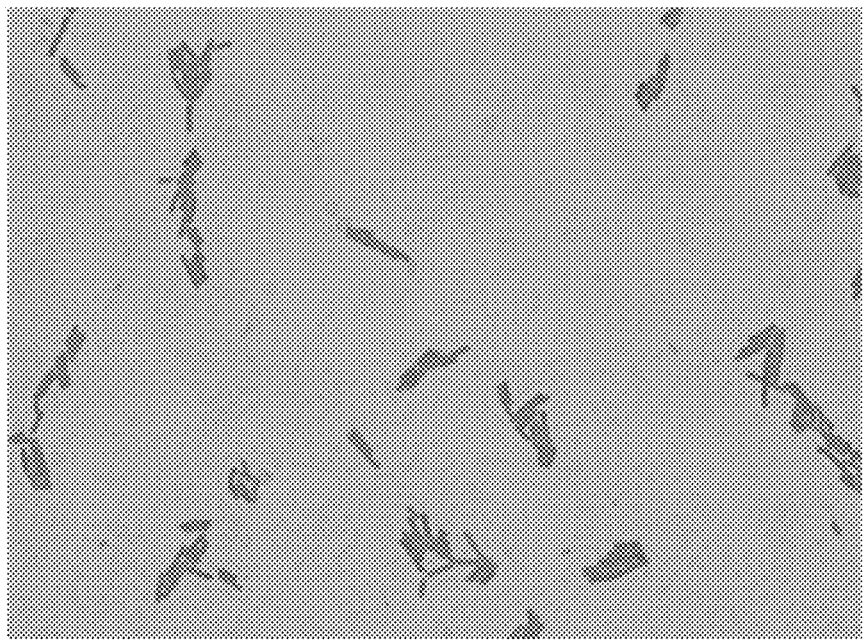
FIG. 2 is a picture (1000×) showing gram-staining of *Megamonas funiformis* AF24-28AC under a microscope.

The colony characteristics of isolated AF24-28AC after culturing for 48 hours in PYG medium is light yellow, flat, with irregular wavy edges and low water content, and about 2-3 mm in diameter (FIG. 1). The mycelium under microscope is rod-shaped, Gram-negative, and does not produce spores and flagella (FIG. 2). The AF24-28AC was detected to be negative to catalase and oxidase. The AF24-28AC on carbon source utilization was detected by API 20A (Mérieux, France), with results shown in Table 1, in which "+" indicates a positive reaction, "−" indicates a negative reaction and "w" indicates a weak positive reaction.

TABLE 1

| Nos. | Reaction | Result |
|---|---|---|
| 1 | production of indole | − |
| 2 | urea (urease) | − |
| 3 | glucose | + |
| 4 | mannitol | + |
| 5 | lactose | + |
| 6 | sucrose | + |
| 7 | maltose | + |
| 8 | salicyl alcohol | + |
| 9 | xylose | + |
| 10 | arabinose | + |
| 11 | Gelatin hydrolysis | − |
| 12 | esculin | − |
| 13 | glycerinum | + |
| 14 | cellobiose | w |
| 15 | mannose | + |
| 16 | melezitose | w |
| 17 | raffinose | + |
| 18 | sorbitol | + |
| 19 | rhamnose | w |
| 20 | trehalose | + |

1.2 Antibiotic Sensitivity of AF24-28AC

The sensitivity of AF24-28AC to 20 common antibiotics was tested by the drug sensitive paper method. 100 µl of AF24-28AC bacterial solution cultured to the logarithmic phase was spread plated. Antibiotic susceptibility papers (purchased from Hangzhou Microbial Reagent Co. LTD.) were affixed on the medium surface of plates, cultured at 37° C. for 48 hours, after which the size of inhibition zone was measured. The results are shown in Table 2.

TABLE 2

| Antibiotics | Diameter of inhibition zone (cm) | Antibiotics | Diameter of inhibition zone (cm) |
|---|---|---|---|
| Penicillin | 0.0 | Ceftriaxone Sodium | 1.0 |
| Oxacillin | 0.0 | Cefoperazone | 0.0 |
| Ampicillin | 1.0 | Amikacin Δ | 2.6 |
| Carbenicillin | 1.2 | Gentamicin | 1.7 |
| Kanamycin | 1.8 | Ceftazidime Δ | 2.0 |
| Cefalexin | 2.2 | Neomycin | 1.3 |
| Cefazolin | 4.0 | Acheomycin | 4.2 |
| Cefradine | 0.8 | Doxycycline | 4.0 |
| Piperacillin | 1.2 | Minocycline Δ | 4.0 |
| Cefuroxime | 3.8 | Erythrocin | 1.3 |

The results show that the AF24-28AC is resistant to penicillin, oxacillin and cefoperazone, and is sensitive to other 17 antibiotics.

Example 2 Biological Activity of *Megamonas funiformis* AF24-28AC

This example mainly examined the generation of metabolites of AF24-28AC after culturing in PYG culture for 48 hours, mainly including the content of short-chain fatty acids (SCFAs) and organic acid products. SCFAs mainly include acetic acid, propionic acid, butyric acid and valeric acid. Organic acids include 3-methyl butyric acid, quinic acid, lactic acid, oxalic acid, malonic acid, benzoic acid, maleic acid, succinic acid, trans-fumaric acid, malic acid, adipic acid, tartaric acid, shikimic acid, citric acid, isocitric acid and L-ascorbic acid. Each of SCFA and organic acid standards was purchased from Sigma. The detection procedure was as follows.

2.1 Sample Pretreatment 1 ml of AF24-28AC bacterial solution was taken and centrifuged at 12000 r/min for 5 mins, followed by collection of the supernatant, which was for detection of short-chain fatty acids (SCFAs) and organic acids.

2.2 Determination of SCFAs

The SCFAs were detected by using the Agilent Meteorological Chromatograph (GC-7890B, Agilent). HP-INNO-Wax (Cross-Linked PEG) capillary column (30 m×0.25 mm×0.25 µm) was used for analysis. The detector was a hydrogen flame ion detector. The parameters of GC were set as follows: column temperature: 180~200° C.; gasification chamber temperature: 240° C.; detection temperature: 210° C.; injection volume: 2 µl; carrier gas flow rate: $N_2$, 50 ml/min; hydrogen flow rate: 50 ml/min; and air flow: 600~700 ml/min.

2.3 Determination of Organic Acids

The organic acids were also detected by the Agilent Meteorological Chromatograph (GC-7890B, Agilent). 122-5532G DB-5 ms column (40 m×0.25 mm×0.25 µm) was used, in which column temperature is 270~290° C., inlet temperature is 250° C. and gas flow rate is 0.86 ml/min.

2.4 Experimental Results

TABLE 3

| Products | acetic acid | formic acid | propionic acid | iso-butyric acid | butyric acid |
|---|---|---|---|---|---|
| Content (mmol/L) | 23.75 | 0 | 48.29 | 0 | 0 |
| Products | isovaleric acid | valeric acid | benzoic acid | 3-methyl butyric acid | quinic acid |

TABLE 3-continued

| Content (mmol/L) | 1.14 | 0.74 | 3.47 | 0.37 | 0 |
|---|---|---|---|---|---|
| Products | lactic acid | oxalic acid | malonic acid | maleic acid | succinic acid |
| Content (mmol/L) | 33.62 | 0 | 0 | 0.04 | 0.06 |
| Products | trans-fumaric acid | malic acid | adipic acid | tartaric acid | shikimic acid |
| Content (mmol/L) | 0 | 0.02 | 0.23 | 0 | 0 |
| Products | citric acid | D,L-isocitric acid trisodium salt | L-Vitamin C | | |
| Content (mmol/L) | 0.13 | 0 | 0 | | |

The results in Table 3 show that the AF24-28AC is capable of producing acetic acid, propionic acid, isovaleric acid, benzoic acid and lactic acid, and can also produce a small amount of valeric acid, 3-methyl butyric acid, maleic acid, succinic acid, malic acid, adipic acid and citric acid.

Example 3 Cholesterol-Lowering Effect of *Megamonas funiformis* AF24-28AC

The method for determining the cholesterol content was performed by using the O-phthalaldehyde colorimetric method (OPA method). The cholesterol-degradation ability of the bacterium was measured by the change of cholesterol content in a medium containing a certain concentration of cholesterol after a time period. The specific method was as follows.

Figure 3:
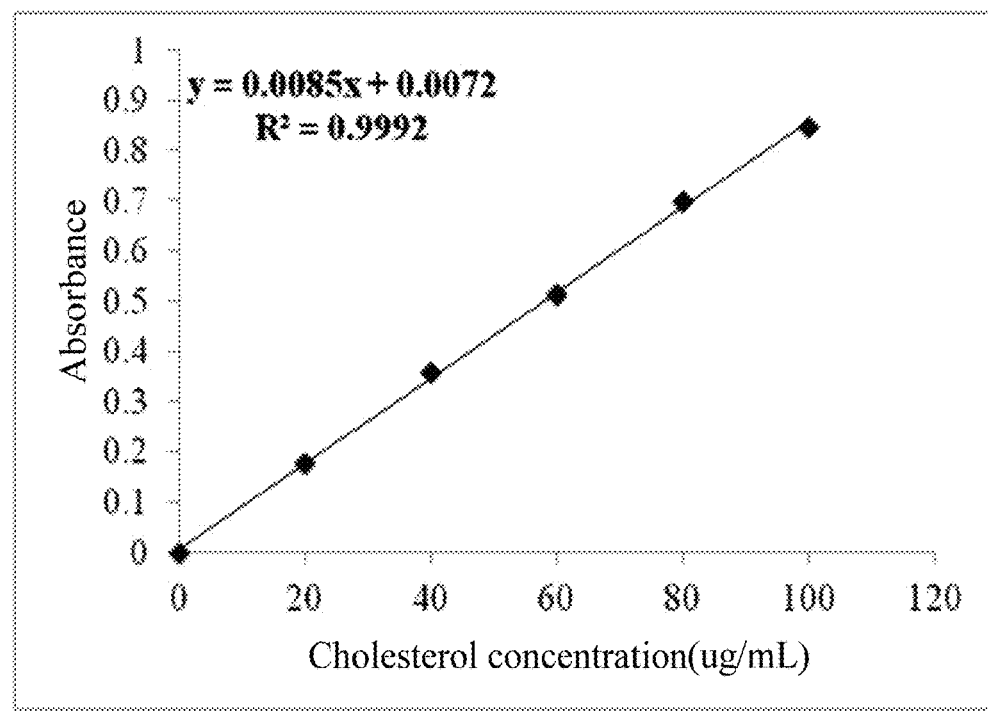
FIG. 3 shows a standard curve for cholesterol detection.

(1) Preparation of Standard Curve 0.5 mg/ml cholesterol standard solutions for 40 µl, 80 µl, 120 µl, 160 µl and 200 µl were accurately measured and respectively placed in clean test tubes. Absolute ethanol was added to make the volume to be 1 ml. 4 ml of O-phthalaldehyde (OPA) (0.5 mg phthalaldehyde in 1 ml glacial acetic acid) was added to each test tube, shaken and mixed, placed for 10 mins at room temperature, followed by addition of 2 ml of concentrated sulfuric acid and stilling for reaction for 10 mins. The absorbance was measured at 550 nm. The standard curve was drawn by using the concentration as the abscissa and the absorbance as the ordinate (FIG. 3). The equation for linear regression was obtained after calculation, that is, y=0.0085x+0.0072, with the correlation coefficient $R^2$ of 0.9992.

(2) Preparation of Cholesterol Medium and Cultivation of Experimental Strains

A certain amount of cholesterol was weighed, dissolved in ethanol at a concentration of 10 mg/ml and then sterilized by filtration. 10 mg/ml autoclaved bile salt, 10% in mass of filtration-sterilized sodium thioglycollate and cholesterol were added to the prepared PYG medium and mixed well. The strain AF24-28AC was inoculated into the medium at an inoculation amount of 3% and cultured in the anaerobic condition at 37° C. for 72 hours.

(3) Determination of Cholesterol

The bacterial solution cultured in PYG medium containing the cholesterol was centrifuged at 10000 r/min, and the supernatant was collected for cholesterol detection. The uninoculated PYG medium containing the cholesterol was used as a blank control. 500 µl of the sample to be tested was placed in a clean test tube, and 3 ml of 95% ethanol and 2 ml of 50% KOH were added, shaken and mixed, then subjected to the saponification reaction in a water bath of 60° C. for 10 mins, and rapidly cooled. 5 ml of n-hexane was added for extraction. 2.5 ml of organic phase was collected to another clean test tube, then dried by nitrogen gas in a water bath of 60° C. 4 ml of solution of 0.5 g/l phthalaldehyde in acetic acid was added for color development for 10 mins. 2 ml of concentrated $H_2SO_4$ was added for 10 mins, and then the absorbance at 550 nm was measured finally.

(4) Calculation of Cholesterol Degradation Rate

The degradation of cholesterol was calculated according to the following formula:

$$L=(A-B)/A\times100\%$$

L: cholesterol degradation rate;
A: cholesterol content in medium containing cholesterol without inoculation;
B: cholesterol content in medium containing cholesterol after bacteria culturing.

(5) Cholesterol Degradation Results

After calculation, the cholesterol degradation rate of AF24-28AC is 68%. It can be seen that the AF24-28AC has the cholesterol degradation ability to some extent.

Example 4 Treatment of *Megamonas funiformis* AF24-28AC on UC Mice

The mouse model selected in this example was an ulcerative colitis mouse model induced by dextran sodium sulfate (DSS, the molecular weight of 36000 to 50000, purchased from MPBIO of USA), which was constructed by continually feeding 0.15% of DSS to mice for 7 days. The C57bl/6 mice used were purchased from Hubei Medical Laboratory Animal Center. They were 8 months, 20 g±2 g in weight and housed in the animal facility of Specific Pathogen Free (SPF) level.

A total of 48 experimental mice were randomly divided into 4 groups, i.e., 12 mice per group, including:

a normal group (control group), in which each mouse was fed with the common feed;

a model group, in which each mouse was intragastrically given with 0.2 ml of phosphate buffer solution (PBS) during DSS modeling;

AF24-28AC treatment group, in which each mouse was intragastrically given with 0.2 ml of AF24-28AC bacterial solution during DSS modeling;

VSL#3 treatment group, in which each mouse was intragastrically given with 0.2 ml of probiotics VSL#3 (purchased from Alfasigma of USA, therapeutic probiotics for UC in clinic) during DSS modeling.

The AF24-28AC treatment process included culturing AF24-28AC bacterial solution for 24 hours, collection of bacterial cells via centrifugation, suspension with phosphate buffer solution (PBS), adjustment of bacteria concentration to $10^9$ cfu/ml, and intragastrical administration of 200 AF24-28AC/day to each mouse. The VSL#3 treatment process also included suspension with phosphate buffer solution (PBS), adjustment of probiotics concentration to $10^9$ cfu/ml, and intragastrical administration of 200 µl VSL#3/day to each mouse.

AF24-28AC and VSL#3 were respectively administered intragastrically to mice at the first 3 days before DSS modeling. DSS was added to the drinking water for mice, and the UC model was constructed by allowing mice receive the drinking water containing DSS ad libitum for 7 days. The body weight, diet and water consumption of mice were recorded daily, and the fecal characteristics and fecal occult blood of mice were observed. The disease activity index (DAI) of mice on day 1, day 3, day 5 and day 7 was calculated according to the DAI scoring standard on Table 4. Mice were sacrificed after completion of experiment, and all mice were subjected to blood sampling, sacrificed by cervical dislocation, collection of colon tissue, photographed, weighed and measurement of colon length. Colon tissue was stored in a refrigerator at −80° C. or in paraformaldehyde.

TABLE 4

DAI Index Scoring Table

| Weight loss (%) | fecal characteristics | fecal occult blood | Score |
|---|---|---|---|
| 0 | normal feces | normal feces | 0 |
| 1-5 | | | 1 |
| 5-10 | loose stool | presence of blood | 2 |
| 10-15 | | | 3 |
| >15 | watery diarrhea | visible bleeding | 4 |

The fecal characteristics in table is specifically described as that the normal feces means the feces is shaped; the loose stool means the feces is viscous and semi-shaped but not adheres to anus; and the watery diarrhea means the feces is watery and can adhere to anus. The fecal occult blood in table is specifically described as that the normal feces means occult blood is negative; the visible bleeding means the feces has red or brown blood; and the presence of blood means the blood is not naked-eye visible but can be detected with tetramethyl benzidine. The DAI index refers to the sum of integral of weight loss, fecal characteristics and fecal occult blood.

In the following, the therapeutic effect of AF24-28AC on DSS-induced UC mouse model was measured by comparison of weight loss, DAI and colon length respectively.

4.1 Weight Changes

Figure 4:
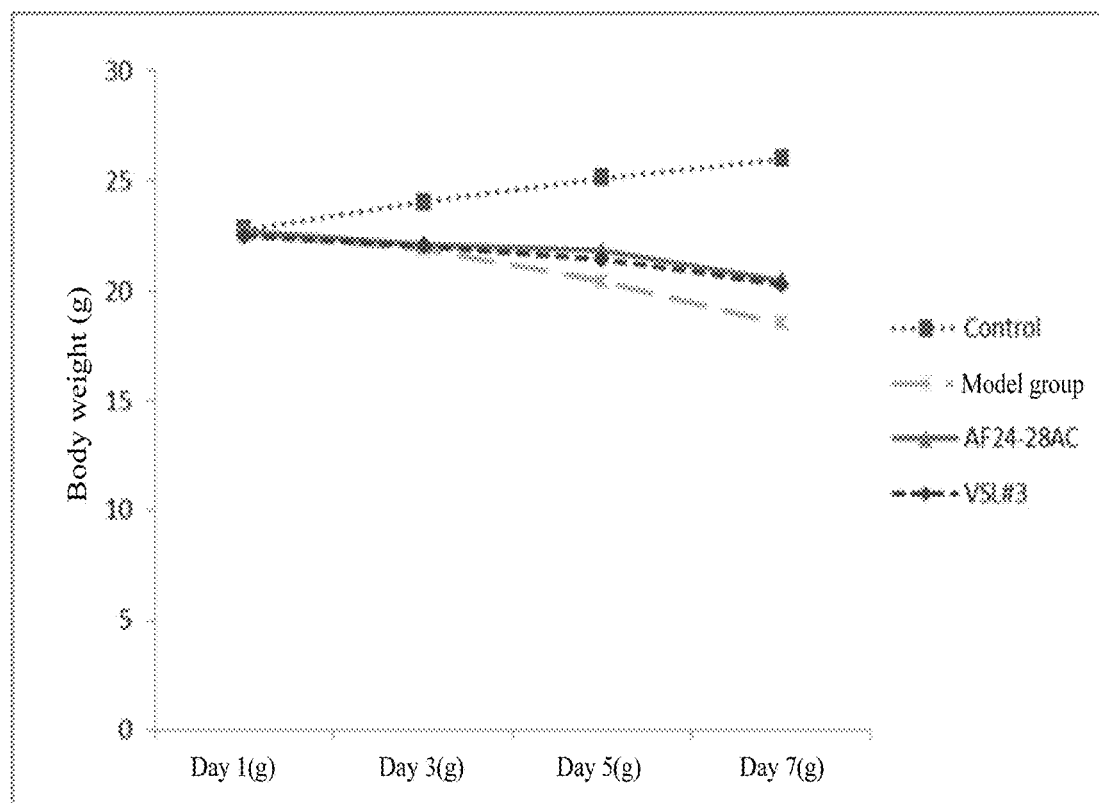
FIG. 4 shows the weight changes of mice in a control group, a model group, VSL#3 treatment group and AF24-28AC treatment group.

The weight changes of mice before and after treatment are shown in Table 5 and FIG. 4 as below:

TABLE 5

| Groups | Day 1 (g) | Day 3 (g) | Day 5 (g) | Day 7 (g) |
|---|---|---|---|---|
| Control group | 22.78 ± 0.62 | 24.03 ± 0.79 | 25.13 ± 1.40 | 25.98 ± 1.57 |
| Model group | 22.56 ± 0.71 | 21.89 ± 0.88* | 20.42 ± 1.43* | 18.51 ± 1.69** |
| AF24-28AC group | 22.72 ± 0.84 | 22.14 ± 0.97 | 21.83 ± 1.42 | 20.47 ± 1.58▲ |
| VSL#3 group | 22.49 ± 0.69 | 22.07 ± 0.89 | 21.41 ± 1.76 | 20.28 ± 1.87▲ |

The results in Table 5 show that the weight of mice in the control group is slowly increased, while the weight of mice in the three DSS-induced groups continues to decrease. On day 3, the weight of mice in the model group began to decrease significantly compared to the control group (*P<0.05). On day 7, the weight difference between the model group and the control group was more significant (**P<0.01). The intervention of AF24-28AC and VSL#3 can slow down the weight loss of UC mice. On day 7, the weight loss of mice in the AF24-28AC and VSL#3 groups was controlled significantly compared to the model group (▲P<0.05). The results show that the AF24-28AC and VSL#3 can control the weight loss caused by UC disease. On day 7, the weight of mice in the AF24-28AC group was slightly higher than the VSL#3 group, indicating that the AF24-28AC is capable of achieving the same effect as VSL#3 on controlling weight loss of UC mice.

4.2 Changes of DAI Index

DAI index of DSS-induced UC mice was changed due to the changes in weight loss, fecal characteristics and fecal occult blood. Changes in DAI index of mice before and after treatment are shown in Table 6 and FIG. 5.

TABLE 6

| Groups | Day 1 | Day 3 | Day 5 | Day 7 |
|---|---|---|---|---|
| Control group | 1.1 ± 0.3 | 1.1 ± 0.7 | 1.2 ± 0.8 | 1.4 ± 0.9 |
| Model group | 1.1 ± 0.5 | 3.4 ± 1.3* | 6.9 ± 1.7** | 9.0 ± 1.9** |
| AF24-28AC group | 1.2 ± 0.3 | 3.2 ± 1.0 | 5.7 ± 0.5▲ | 7.4 ± 1.8▲ |
| VSL#3 group | 1.1 ± 0.4 | 3.3 ± 1.2 | 5.9 ± 1.7 | 7.8 ± 1.8 |

Figure 5:
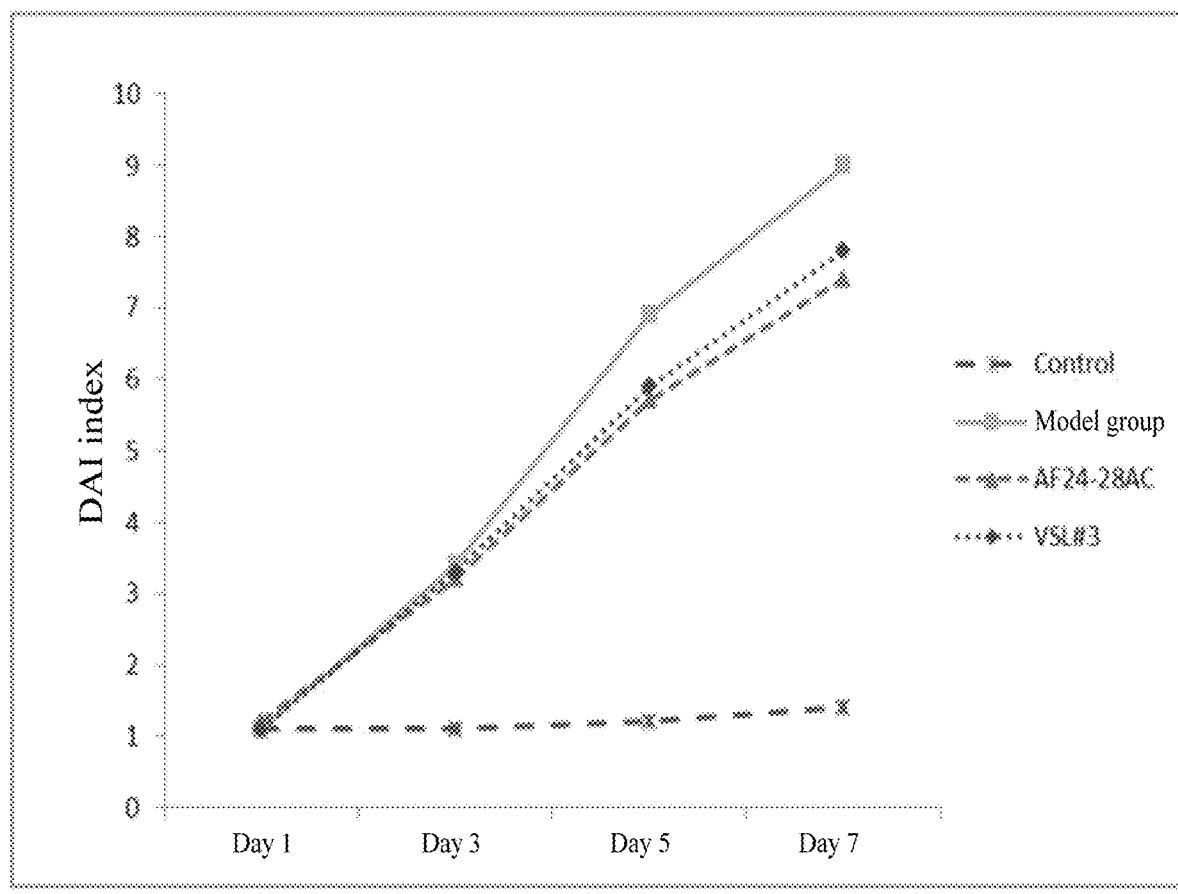
FIG. 5 shows the DAI index changes of mice in a control group, a model group, VSL#3 treatment group and AF24-28AC treatment group.

The data in Table 6 and FIG. 5 show that the DAI of mice in the control group is basically unchanged, while the DAI of mice in the model group, the AF24-28AC and VSL#3 groups is gradually increased with the induction of DSS. On day 3, the DAI of mice in the model group began to increase significantly compared to the control group (*P<0.05). On day 7, the DAI of mice in the model group reached the highest level compared to the control group (**P<0.01). The intervention of the bacterium of the present disclosure can control the increase of DAI, in which the DAI of mice in the AF24-28AC group was significantly controlled on day 5 and day 7 compared to the control group (▲P<0.05), the DAI of mice in the AF24-28AC group was lower than the VSL#3 group, and the VSL#3 group did not exhibit significant effect on controlling DAI. Therefore, the AF24-28AC is better than VSL#3 on controlling the DAI increase of UC mice.

4.3 Changes of Colon Length

The colon tissue of UC model mice can be changed because the ulcers and inflammation cause the shortening of colon tissue. After the treatment, the colon length of mice measured by anatomy is shown in Table 7.

TABLE 7

| Groups | colon length (cm) |
|---|---|
| Control group | 8.14 ± 0.57 |
| Model group | 4.54 ± 0.79** |
| VSL#3 group | 6.10 ± 0.89▲ |
| AF24-28AC group | 6.23 ± 0.91▲ |

The results in Table 7 show that the colon tissue of mice in the model group is shortened significantly 7 days after DSS induction, which is also greatly significant compared to the control group (**P<0.01). The intervention of strain AF24-28AC of the present disclosure and VSL#3 can significantly control the colon shortening of mice, which is very significant compared to the model group (*P<0.01). According to the data in Table 7, it can be seen that the colon length of mice in the AF24-28AC group is longer than that of mice in the VSL#3 group. Therefore, AF24-28AC exhibits a slightly stronger ability on controlling the colon shortening of UC mice than the VSL#3. It can be seen that the strain AF24-28AC of the present disclosure can significantly alleviate the colon lesions in mice, which has an equal or even better efficacy compared to VSL#3.

Example 5 Food Composition Containing Megamonas funiformis AF24-28AC

Raw materials and proportion thereof were shown in Table 8.

TABLE 8

| Raw material(s) | Mass percentage (%) |
| --- | --- |
| Meganionas funiformis AF24-28AC | 0.5 |
| milk | 90.0 |
| sugar | 9.0 |
| Vitamin C | 0.5 |

Milk and sugar in proportion of formula as above were mixed, stirred to complete mixture, preheated, homogenized at the pressure of 20 Mpa, and then sterilized at about 90° C. for 5 to 10 mins, cooled to 40 to 43° C., followed by adding a protective agent (Vitamin C) and inoculation of $1\text{-}100\times10^6$ cfu/g Megamonas funiformis AF24-28AC, thus obtaining the food composition containing Megamonas funiformis AF24-28AC.

Example 6 Pharmaceutical Composition Containing Megamonas funiformis AF24-28AC

Raw materials and proportion thereof were shown in Table 9.

TABLE 9

| Raw material(s) | Mass percentage (%) |
| --- | --- |
| Meganionas funiformis AF24-28AC | 1.0% |
| lactose | 2.0% |
| yeast powder | 2.0% |
| peptone | 1.0% |
| purified water | 93.5% |
| vitamin C | 0.5% |

Lactose, yeast powder and peptone in proportion were mixed with purified water to be uniform, preheated to 60 to 65° C., homogenized at the pressure of 20 Mpa, and then sterilized at about 90° C. for 20 to 30 mins, cooled to 36 to 38° C., followed by adding vitamin C and inoculation of $1\text{-}50\times10^6$ cfu/mL active Megamonas funiformis AF24-28AC, after which fermented at 36 to 38° C. to pH 6.0, centrifuged, freeze-dried to less than 3% of water content, thus obtaining a freeze-dried product containing Megamonas funiformis AF24-28AC. 0.5 g of the freeze-dried product containing Megamonas funiformis AF24-28AC was weighed, mixed with an equal amount of maltodextrin and a protective agent (such as vitamin C, cysteine), and then encapsulated into capsules, thus obtaining the pharmaceutical composition containing Megamonas funiformis AF24-28AC.

Example 7 Manufacture of a Medicament for Treating Inflammation-Related Diseases Such as Ulcerative Colitis (UC)

7.1 Preparation of Bacterial Solution

Megamonas funiformis AF24-28AC ($1\times10^9$ cfu/ml) were anaerobically fermented in the PYG medium at 37° C. for 2 to 3 days.

7.2 Preparation of Growth Factors

The skimmed milk and casein were mixed, centrifuged and ultra-filtered to obtain a crude extract of milk growth factor, including nutrients of vitamins, purines and/or pyrimidines.

7.3 Manufacture of Medicament or Pharmaceutical Dosage Form 5 volumes (ml) of growth factor and 1 volume (ml) of protective agent (such as vitamin C, cysteine) were added to 100 volumes (ml) of the fermented bacterial solution of Megamonas funiformis AF24-28AC, fully stirred to be uniform, and then added with starch excipients (such as maltodextrin), thus obtaining the medicament or pharmaceutical dosage form containing Megamonas funiformis AF24-28AC.

Example 8 Manufacture of a Medicament for Treating Cardiovascular Diseases Such as Hyperlipidemia 8.1 Preparation of Bacterial Solution Megamonas funiformis AF24-28AC ($1\times10^9$ cfu/ml) were anaerobically fermented in the PYG medium at 37° C. for 2 to 3 days.

8.2 Preparation of Growth Factors

The skimmed milk and casein were mixed, centrifuged and ultra-filtered to obtain a crude extract of milk growth factor, including nutrients of vitamins, purines and/or pyrimidines.

8.3 Manufacture of Medicament or Pharmaceutical Dosage Form 5 volumes (ml) of growth factor and 1 volume (ml) of protective agent (such as vitamin C, cysteine) were added to 100 volumes (ml) of the fermented bacterial solution of Megamonas funiformis AF24-28AC, fully stirred to be uniform, and then added with starch excipients (such as maltodextrin), thus obtaining the medicament or pharmaceutical dosage form containing Megamonas funiformis AF24-28AC.

All publications mentioned herein are incorporated by reference as if each individual document was cited as a reference in the present application. It should also be understood that, after reading the above teachings of the present disclosure, those skilled in the art can make various changes or modifications, equivalents of which falls in the scope of claims as defined in the appended claims.

What is claimed is:

1. A method for treating ulcerative colitis comprising administering a pharmaceutically effective amount of biologically pure *Megamonas funiformis* or a composition comprising the biologically pure *Megamonas funiformis* to a subject in need of treatment for the ulcerative colitis,
wherein the biologically pure *Megamonas funiformis* has a sequence of 16s rDNA as shown in SEQ ID NO.:1.

2. The method according to claim 1, wherein the biologically pure *Megamonas funiformis* is *Megamonas funiformis* AF24-28AC with a deposit number of GDMCC 60093.

3. The method according to claim 1, wherein the biologically pure *Megamonas funiformis* is capable of one or more selected from the group consisting of:
   (i) lowering blood lipid levels in a mammal;
   (ii) controlling weight loss in a mammal;
   (iii) decreasing disease activity index (DAI) in a mammal; and
   (iv) relieving intestinal lesions in a mammal.

4. The method according to claim 1, wherein the composition is administered orally.

5. The method according to claim 1, wherein the administration dosage is 0.01 to 5 g/50 kg body weight per day.

6. The method according to claim 1, wherein the composition is in a unit dosage form of one tablet, one capsule or one vial, and the composition in each unit dosage form is of the weight from 0.05 to 5 g.

7. The method according to claim 1, wherein the composition further comprises a food acceptable or pharmaceutically acceptable carrier.

8. The method according to claim 1, wherein the composition further comprises probiotics and/or prebiotics.

9. The method according to claim 1, wherein the composition further comprises a substance capable of maintaining the viability of *Megamonas funiformis*.

10. The method according to claim 1, wherein the composition further comprises a growth factor.

* * * * *